(12) United States Patent
Beebe et al.

(10) Patent No.: US 7,277,021 B2
(45) Date of Patent: Oct. 2, 2007

(54) DEVICE AND METHOD FOR ALERTING A RUNNER WHEN A NEW PAIR OF RUNNING SHOES IS NEEDED

(75) Inventors: David J. Beebe, Monona, WI (US);
Brian E. Schwartz, Riverside, IL (US);
Steven J. Pauls, Sheboygan, WI (US);
Timothy D. Rand, Madison, WI (US);
Brant R. Kochsiek, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 410 days.

(21) Appl. No.: 11/033,370

(22) Filed: Jan. 11, 2005

(65) Prior Publication Data

US 2006/0152377 A1 Jul. 13, 2006

(51) Int. Cl.
*G08B 19/00* (2006.01)
*G08B 21/00* (2006.01)
*G08B 23/00* (2006.01)
*G01M 19/00* (2006.01)
*G01L 1/22* (2006.01)
*A43B 5/00* (2006.01)
*A43B 23/00* (2006.01)

(52) U.S. Cl. ............ 340/665; 340/517; 340/521; 340/522; 340/573.1; 73/172; 73/760; 73/862.045; 73/862.046; 36/83; 36/114; 36/132; 36/137

(58) Field of Classification Search ........ 340/517–522, 340/665–666, 573.1; 73/172, 760, 862.045, 73/862.046; 36/83–137
See application file for complete search history.

(56) References Cited

U.S. PATENT DOCUMENTS

| | | | | |
|---|---|---|---|---|
| 5,268,081 A | * | 12/1993 | Dousek ...................... 204/237 |
| 5,323,650 A | * | 6/1994 | Fullen et al. ................. 73/172 |
| 5,373,651 A | | 12/1994 | Wood .......................... 36/114 |
| 5,471,405 A | * | 11/1995 | Marsh .......................... 702/41 |
| 5,513,448 A | | 5/1996 | Lyons ........................... 36/28 |
| 5,813,142 A | * | 9/1998 | Demon .......................... 36/29 |
| 5,894,682 A | | 4/1999 | Broz ............................. 36/31 |
| 5,914,659 A | * | 6/1999 | Herman et al. .......... 340/573.1 |
| 5,918,502 A | * | 7/1999 | Bishop ........................ 73/172 |
| 5,929,332 A | | 7/1999 | Brown ......................... 73/172 |
| 5,945,911 A | * | 8/1999 | Healy et al. ............ 340/573.1 |
| 6,087,926 A | * | 7/2000 | Hajianpour .............. 340/573.1 |
| 6,122,846 A | * | 9/2000 | Gray et al. ................... 36/136 |
| 6,160,254 A | * | 12/2000 | Zimmerman et al. ....... 250/225 |
| 6,186,000 B1 | * | 2/2001 | Kaneko et al. ............... 73/172 |
| 6,243,971 B1 | | 6/2001 | Hofft ......................... 36/50.1 |
| 6,289,743 B1 | | 9/2001 | Norton ....................... 73/847 |
| 6,578,291 B2 | | 6/2003 | Hirsch et al. ................. 36/132 |
| 6,807,869 B2 | * | 10/2004 | Farringdon et al. .... 73/862.046 |

* cited by examiner

*Primary Examiner*—Benjamin C. Lee
*Assistant Examiner*—Lam Pham
(74) *Attorney, Agent, or Firm*—Boyle Fredrickson S.C.

(57) ABSTRACT

A device and method are provided for determining the wear of a sole of a shoe. The device includes first and second sensors receivable in the sole of the shoe. The sensors are axially spaced and generate signals in response to corresponding impact forces acting thereon. A control circuit is connectable to the first and second sensors. The control circuit compares the difference between the first and second signals to a threshold and generates an alert signal in response to the difference between the first and second signal meeting the threshold.

20 Claims, 3 Drawing Sheets

DEVICE AND METHOD FOR ALERTING A RUNNER WHEN A NEW PAIR OF RUNNING SHOES IS NEEDED

FIELD OF THE INVENTION

This invention relates generally to athletic shoes, and in particular, to a device and method for measuring the wear of a sole of a running shoe in a quantitative manner and for alerting the runner when a new pair of shoes is needed.

BACKGROUND AND SUMMARY OF THE INVENTION

It is a fact of life that the shoes of an individual will eventually become old and wear out. For those who are not avid runners, the terms 'get old' and 'wear out' are often associated with the appearance of a particular pair of shoes. However, for the avid runner, this is not always the case. Many running injuries are caused by the continued use of improper or worn running shoes. An increase in the number of incidences of injury can be directly correlated to the degradation of the materials within the sole of a running shoe. Unfortunately, shoes that have been worn past their useful life do not always appear worn, especially if those shoes are only used for running. In fact, it is nearly impossible to tell if a shoe has been worn beyond its useful life based on appearance alone.

As is known, the average running shoe lasts between 300 and 500 miles before the soles of the shoes begin to degrade. This threshold is dependant on several factors such as the size of the person wearing them or the wearer's running style. As heretofore described, when the sole of the shoe begins to degrade, the risk for injury to the runner can increase significantly. Nevertheless, there is no mechanism for advising a runner that a shoe is worn out. Presently, the runner has two options for determining if a pair of shoes has worn out. The first option is to keep a log of the miles run in a pair of shoes and to know how many miles a pair of shoes typically lasts from past experience. The second option a runner uses to determine if a pair of shoes has worn out is the feel of the shoes. Avid runners can sometimes determine that a pair of shoes is becoming worn by feeling extra soreness in their muscles or joints after a run. It can be appreciated that there are flaws in both of these prior methods. Therefore, it is highly desirable to provide a device that can measure the wear of a shoe sole in a quantitative manner and alert a runner when a new pair of shoes is needed.

Therefore, it is a primary object and feature of the present invention to provide a device and method for measuring the wear of a sole of a shoe in a quantitative manner and for alerting a runner when a new pair of shoes is needed.

It is a further object and feature of the present invention to provide a device for measuring the wear of a sole of a shoe that may be easily incorporated into a standard running shoe.

It is a still further object and feature of the present invention to provide a device and a method for measuring the wear of a sole of a shoe that are inexpensive and simple to utilize.

In accordance with the present invention, a device is provided for determining the wear of a sole of a shoe. The device includes a first sensor that is receivable in the sole of the shoe. The first sensor generates a first signal in response to a first impact force thereon. A second sensor is also receivable in the sole of the shoe. The second sensor generates a second signal in response to a second impact force thereon. A control circuit is connectable to the first and second sensors. The control circuit generates an alert signal in response to the first and second signals.

It is contemplated for the first and second sensors to be pressure sensors and for the control circuit to include a first amplifier for amplifying the first signal and a second amplifier for amplifying the second signal. The control circuit also includes a differential amplifier for determining a difference between the first amplified signal and the second amplified signal and for amplifying the difference between the first amplified signal and the second amplified signal. In addition, the control circuit includes a comparator for comparing the amplified difference between the first amplified signal and the second amplified signal with a threshold and for generating an illumination signal if the amplified difference between the first amplified signal and the second amplified signal meets the threshold. A light emitting diode generates the alert signal in response to the illumination signal.

In accordance with a further aspect of the present invention, a device is provided for determining the wear of a sole of a shoe. The device includes a first pressure sensor receivable in the sole of the shoe. The first sensor generates a first signal that is proportional to a first impact force acting thereon. A second pressure sensor is also receivable in the sole of the shoe at a location axially spaced from the first pressure sensor. The second sensor generates a second signal that is proportional to a second impact force acting thereon. A control circuit is connectable to the first and second pressure sensors. The control circuit compares the difference between the first and second signals to a threshold and generates an alert signal in response to the difference between the first and second signal meeting the threshold.

It is contemplated for the control circuit to include a first amplifier for amplifying the first signal and a second amplifier for amplifying the second signal. The control circuit also includes a differential amplifier for determining a difference between the first amplified signal and the second amplified signal and for amplifying the difference between the first amplified signal and the second amplified signal. In addition, the control circuit includes a comparator for comparing the amplified difference between the first amplified signal and the second amplified signal with a threshold and for generating an illumination signal if the amplified difference between the first amplified signal and the second amplified signal meets the threshold. A light emitting diode generates the alert signal in response to the illumination signal.

In accordance with a still further aspect of the present invention, a method is provided for measuring the wear of a sole of a shoe. The method includes the steps measuring an impact force exerted on a first portion of the shoe and measuring an impact force exerted on a second portion of the shoe. The impact force exerted on the first portion of the shoe is compared with the impact force exerted on the second portion of the shoe. Thereafter, an alert signal is generated if the difference between the impact force exerted on the first portion of the shoe and the impact force exerted on the second portion of the shoe meets a threshold. A light emitting diode is illuminated in response to the alert signal.

The sole of the shoe includes a midsole affixed to an upper surface of an outsole. The method of the present invention may include the additional steps of positioning a first sensor between the outsole and the midsole to measure the impact force exerted on the first portion of the shoe and positioning a second sensor on an upper surface of the midsole to measure the impact force exerted on the second portion of the shoe. The first sensor and the second sensor are axially aligned.

The step of comparing the impact force exerted on the first portion of the shoe and the impact force exerted on the second portion of the shoe may include the additional steps of generating a first signal that is proportional to a first impact force and generating a second signal that is proportional to a second impact force acting thereon. Thereafter, the first and second signals are amplified. The difference between the first amplified signal and the second amplified signal is determined.

A control circuit is provided to compare the impact force exerted on the first portion of the shoe and the impact force exerted on the second portion of the shoe and to generate the alert signal. The control circuit is enclosed in a capsule which may be interconnected to the shoe.

BRIEF DESCRIPTION OF THE DRAWINGS

The drawings furnished herewith illustrate a preferred construction of the present invention in which the above advantages and features are clearly disclosed as well as others which will be readily understood from the following description of the illustrated embodiment.

In the drawings.

DETAILED DESCRIPTION OF THE DRAWINGS

Figure 1:
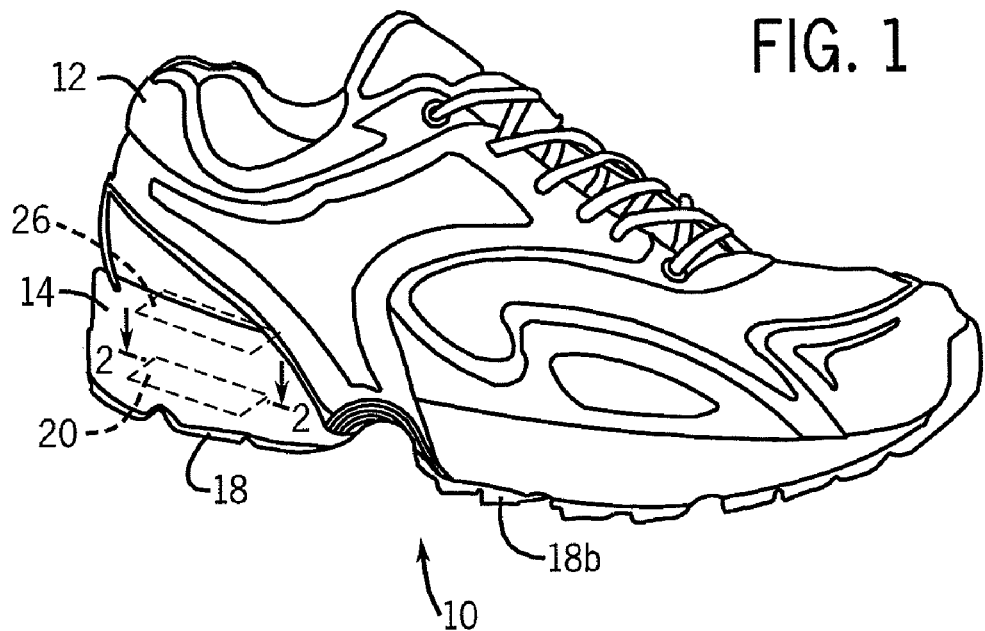
FIG. 1 is an isometric view of a running shoe incorporating a device for alerting a runner when a new pair of running shoes is needed.
Figure 2:
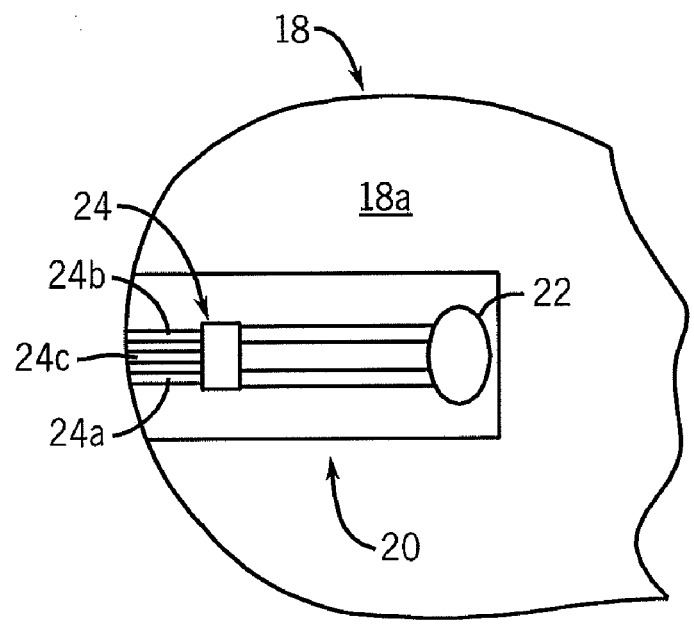
FIG. 2 is a cross sectional view of the running shoe incorporating a device for alerting a runner when a new pair of running shoes is needed taken along line 2-2 of FIG. 1.
Figure 3:
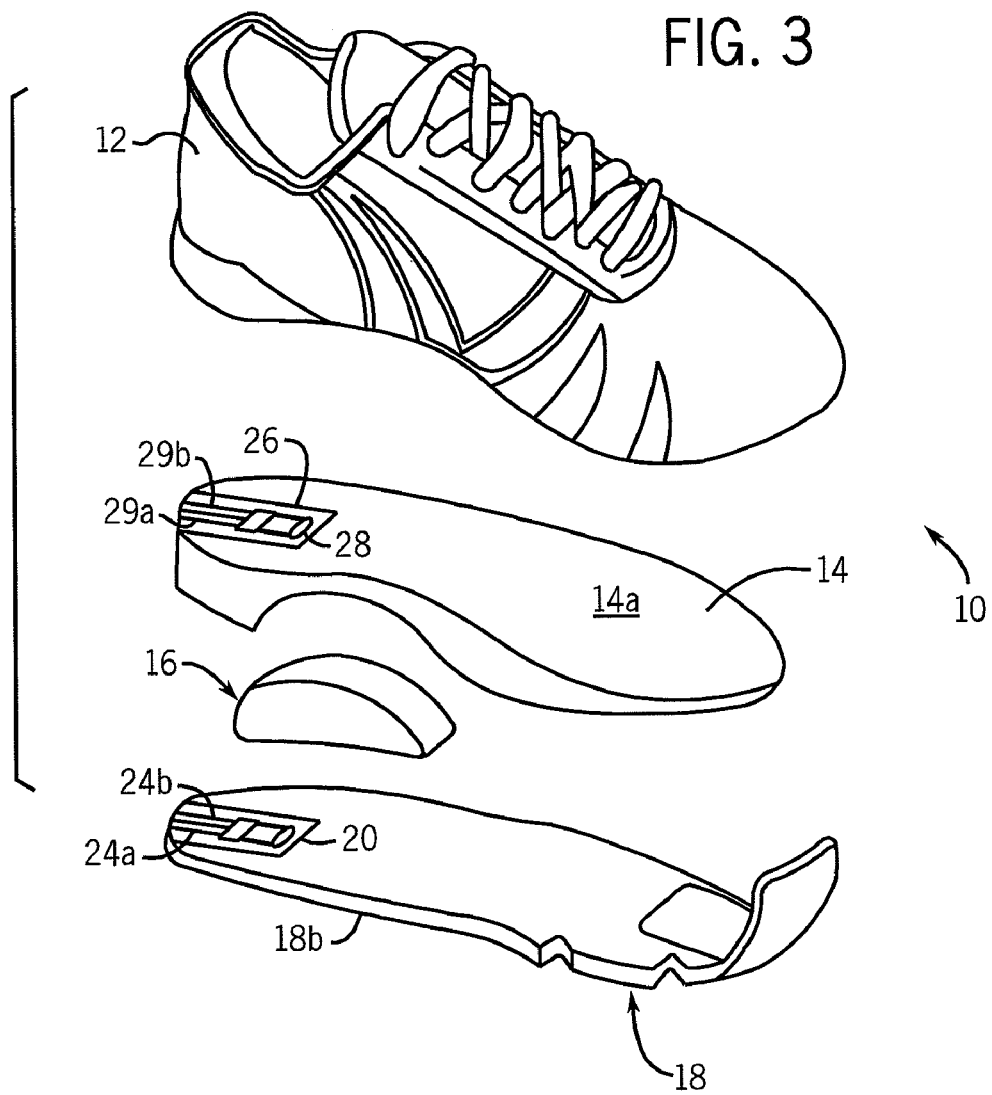
FIG. 3 is an exploded view of the running shoe of FIG. 1.

Referring to FIGS. 1-3, an exemplary running shoe for use with the device and method of the present invention is generally designated by the reference numeral 10. As is conventional, running shoe 10 is constructed from four elements: upper 12, midsole 14, footbridge or arch 16 and outsole 18. Upper 12 is typically formed from leather, nylon, or vinyl depending on the quality of running shoe 10. Footbridge 14 is fabricated from a plastic or foam material and outsole 18 is fabricated of hard rubber.

Midsole 14 of running shoe 10 is typically fabricated from a combination of foamed copolymers such as ethylene and vinyl acetate (EVA) and polyurethane (PU). As is known, when a force is exerted on the copolymers of midsole 14, there is a reduction of the air content in the foam cells and the copolymers are compressed. During a long run, the foamed copolymers in midsole 14 are repeatedly compressed under the force of the runner's foot. It has been found that the foamed copolymers of midsole 14 do not fully recover after such runs. This loss of air content relates directly to a decrease in the elasticity of the materials. With loss of air content, midsole 14 begins breaking down structurally, causing unwanted stresses in the joints of the runner, especially the knee.

Midsole 14 of running shoe 10 wears according to the striking pattern of lower surface 18b of outsole 18 of running shoe 10 with the running surface on which running shoe 10 is used. For example, a forefoot striker is more often a short-distance runner, but about five percent of the running population has adapted this style for long distance. This type of runner will wear 14 midsole directly under the ball of the foot first. An overpronator runner severely rolls their foot over when striding, causing midsole 14 to wear at a localized area over the inside portion of the ball of the foot and at the back of the heel where the runner's foot first contacts the running surface. The neutral striking runner will wear out midsole 14 under the ball of the foot like the forefoot striker, but in addition, will wear out the heel region like the overpronator. The last wear pattern occurs in the supinator runner who pronates very little. Typically the supinator runner will wear the outside portion of midsole 14 of the forefoot and the heel respectively.

The main wear points of midsole 14 of running shoe 10 occur where the runner's foot exerts the most pressure on midsole 14. As the foot makes the first impact with the running surface, there is a spike in pressure at the heel of running shoe 10. When the foot pronates forward and pushes off, the ball of the foot and the big toe experience similar spikes in pressure. This is a second main wear point in the shoe. The position of the pressure at the ball of the foot depends upon the specific striking pattern of the runner: the neutral runner experiences this pressure at the middle to inner portion of the ball of the foot; the supinator experiences this pressure at the middle to outer portion of the ball of the foot; and the overpronator experiences this pressure at the inside portion of the ball of the foot.

Since the main wear point of midsole 14 of running shoe 10 corresponds to the area of midsole 14 below the heel of the runner, it is contemplated to measure the degradation of midsole 14 at such location. In order to measure the degradation of midsole 14, first sensor 20 is positioned between upper surface 18a of outsole 18 of running shoe 10 and lower surface 14b of midsole 14. It is contemplated for first sensor 20 to generate a signal corresponding to the forces exerted thereon that are perpendicular to the plane in which sensor 20 lies. By way of example, first sensor 20 may take the form of a Flexi-Force Sensor, Model Number A201, manufactured by Tekscan, Inc., but other types of sensors are possible without deviating from the scope of the present invention.

First sensor 20 is constructed of two layers of a substrate, such as a polyester film. On each layer, a conductive material such as silver is applied, followed by a layer of pressure-sensitive ink. Adhesive is then used to laminate the two layers of the substrate together. Circle 22 on top of the pressure-sensitive ink defines the sensing region of first sensor 20. Silver extends from sensing region 22 to corresponding connector 24 at the opposite end of first sensor 20 to form conductive leads. Connector 24 may take the form of solderable, male square pin connector, which allows connector 24 to be incorporated into a circuit. Connector 24 includes two outer pins 24a and 24b that are active and center pin 24c that is inactive. In operation, first sensor 20 acts as a variable resistor in an electrical circuit. When first sensor 20 is unloaded, the resistance of first sensor is very high (greater than 5 Meg-ohm). When a force is applied to sensing region 22 of first sensor 20, the resistance decreases. As best seen in FIG. 2, sensing region 22 is parallel to upper surface 18a of outsole 18 and is placed directly below the region in the shoe where the heel of a runner would apply pressure.

Second sensor 26 is positioned between upper surface 14a of midsole 14 of running shoe 10 and lower surface 12b of upper 12. Similar to first sensor 20, it is contemplated for second sensor 26 to generate a signal corresponding to the forces exerted thereon that are perpendicular to the plane in which second sensor 22 lies. By way of example, second sensor 26 may take the form of a Flexi-Force Sensor, Model Number A201, manufactured by Tekscan, Inc., but other types of sensors are possible without deviating from the scope of the present invention.

Second sensor 26 is constructed of two layers of a substrate, such as a polyester film. On each layer, a conductive material such as silver is applied, followed by a layer of pressure-sensitive ink. Adhesive is then used to laminate the two layers of substrate together. Circle 28 on top of the pressure-sensitive ink defines the sensing region of second sensor 26. Silver extends from sensing region 28 to a corresponding connector at the opposite end of second sensor 26 to form conductive leads. The connector may take the form of solderable, male square pin connector, which allows the connector to be incorporated into a circuit. The connector includes two outer pins 29a and 29b that are active and a center pin that is inactive. In operation, second sensor 26 acts as a variable resistor in an electrical circuit. When second sensor 26 is unloaded, the resistance of second sensor 26 is very high (greater than 5 Meg-ohm). When a force is applied to sensing region 28 of second sensor 26, the resistance decreases. As best seen in FIG. 3, sensing region 28 is parallel to upper surface 14a of midsole 14 and is placed directly below the region in the shoe where the heel of a runner would apply pressure in axial alignment with first sensor 20.

While it is contemplated for first and second sensors 20 and 26, respectively, to be vertically aligned, for reasons hereinafter described, the horizontal location of first and second sensors 20 and 26, respectively, can be varied without deviating from the scope of the present invention. For example, first and second sensors 20 and 26, respectively, may be positioned in running shoe 10 under the balls of a runner's foot. Further, while first and second sensors 20 and 26, respectively, are described as being positioned adjacent corresponding lower and upper surfaces 14b and 14a of midsole 14, other locations in running shoe 10 are possible without deviating from the scope of the present invention. It is noted that by positioning first and second sensors 20 and 26, respectively, adjacent corresponding lower and upper surfaces 14b and 14a of midsole 14, the manufacture of running shoe 10 is simplified.

Figure 4:
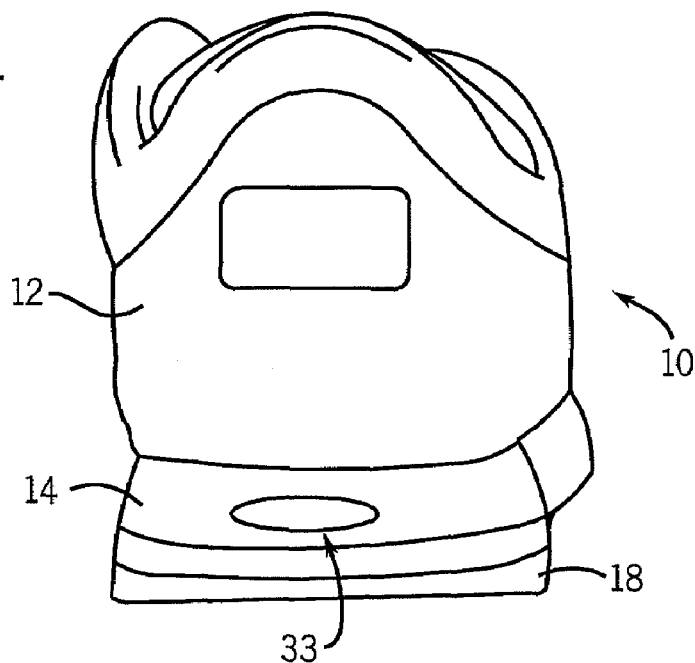
FIG. 4 is an end view of the running shoe of FIG. 1.
Figure 5:
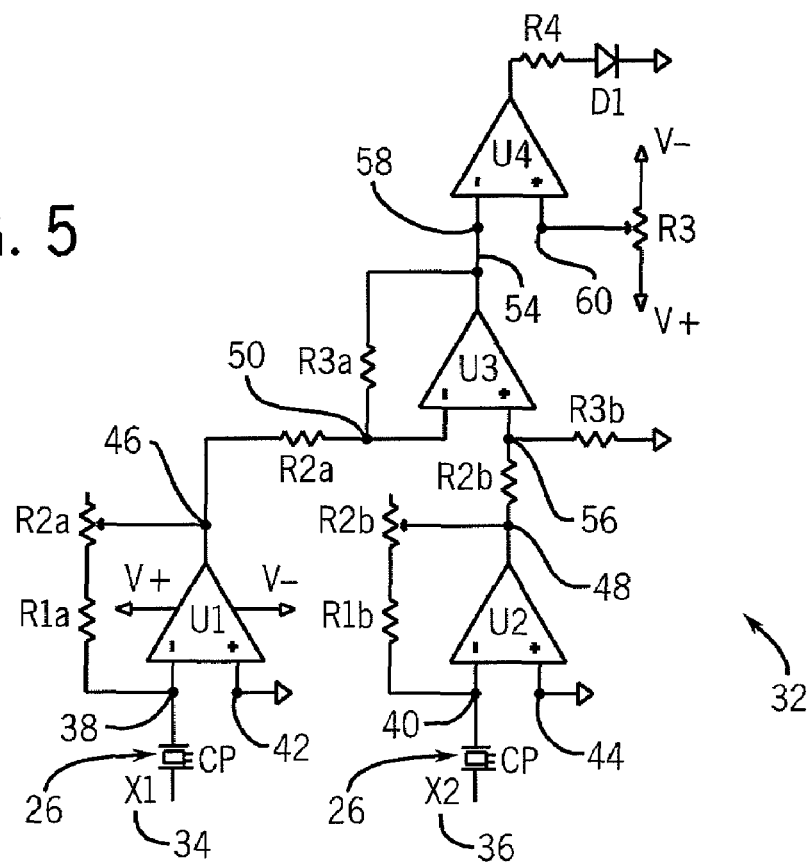
FIG. 5 is a schematic view of an alert circuit for use with the running shoe of FIG. 1.

Referring to FIG. 5, first and second sensors 20 and 26, respectively, are operatively connected to an alert circuit, generally designated by the reference numeral 32. By way of example, alert circuit 32 may be enclosed in plastic casing 33 that may be separated from or interconnected to running shoe 10, FIG. 4. More specifically, outer pins 24a and 29a are interconnected to corresponding voltage sources 34 and 36, respectively, and outer pins 24b and 29b are interconnected to first inputs 38 and 40, respectively, of differential amplifiers U1 and U2, respectively. In addition, outer pin 24b is interconnected to output 46 of differential amplifier U1 through resistor R1a and potentiometer P2a and outer pin 29b is interconnected to output 48 of differential amplifier U2 through resistor R1b and potentiometer P2b. Second inputs 42 and 44 of differential amplifiers U1 and U2, respectively, are connected to ground.

Output 46 of differential amplifier U1 is connected to first input 50 of differential amplifier U3 by resistor R2a. In addition, first input 50 of differential amplifier U3 is connected to output 54 of differential amplifier U3 by resistor R3a. Output 48 of differential amplifier U2 is connected to second input 56 of differential amplifier U3 by resistor R2b. In addition, second input 56 of differential amplifier U3 is connected to ground by resistor R3b.

Output 54 of differential amplifier U3 is connected to first input 58 of differential amplifier U4. Second input 60 of differential amplifier U4 is connected to the output of potentiometer P3 that acts as a voltage divider between predetermined voltage potentials. Output 64 of differential amplifier U4 is connected to ground through resistor R4 and light emitting diode D1.

It can be appreciated that midsole 14 of running shoe 10 is intended to absorb the impact associated with walking or running. Therefore, first sensor 20 positioned between upper surface 18a of outsole 18 of running shoe 10 and lower surface 14b of midsole 14 will sense virtually the full amount of impact force associated with each step of a runner. That force will then be dispersed throughout the shoe sole lessening the impact on a wearer's foot. As a result, second sensor 26 positioned between upper surface 14a of midsole 14 of running shoe 10 and lower surface 12b of upper will sense a much smaller force.

As midsole 14 of running shoe 10 wears, the foamed copolymers in midsole 14 become less elastic and less effective in dispersing the impact forces associated with each step of the runner. Consequently, while the impact force on first sensor 20 remains the same, the impact force experienced by second sensor 26 will increase. As a result, the difference between the impact forces experienced by first and second sensors 20 and 26, respectively, will decrease as midsole 14 of running shoe 10 wears.

Referring back to FIG. 5, it can be appreciated that the first two stages of alert circuit 32 are identical for first and second sensors 20 and 26, respectively. As a result, outputs 46 and 48 of differential amplifiers U1 and U2, respectively, have identical load-voltage responses. Differential amplifier U3 produces a signal at output 54 equal to a proportion of the impact forces sensed by first and second sensors 20 and 26, respectively, magnified by a predetermined gain of differential amplifier U3. Differential amplifier U4 compares the signal at output 54 of differential amplifier to a benchmark 'failure' voltage that corresponds to a ratio the impact forces sensed by first and second sensors 20 and 26, respectively, that demonstrates an amount of shoe wear that would require the user to buy a new pair of shoes. As such, when output 54 of differential amplifier U3 matches the benchmark 'failure' voltage, LED D1 illuminates so as to alert the runner that running shoe 10 should no longer be used.

Various modes of carrying out the invention are contemplated as being within the scope of the following claims particularly pointing out and distinctly claiming the subject matter that is regarded as the invention.

We claim:

1. A device for determining the wear of a sole of a shoe, comprising:
   a first sensor receivable in the sole of the shoe, the first sensor generating a first signal in response to a first impact force thereon;
   a second sensor receivable in the sole of the shoe at a location vertically spaced from the first sensor, the second sensor generating a second signal in response to a second impact force thereon; and
   a control circuit connectable to the first and second sensors, the control circuit determining a difference between the first and the second sensor signals, generating an alert signal in response to the difference meeting a predefined criteria.

2. The device of claim 1 wherein the first sensor is a pressure sensor.

3. The device of claim 2 wherein the second sensor is a pressure sensor.

4. The device of claim 1 wherein the control circuit includes:
   a first amplifier for amplifying the first signal; and
   a second amplifier for amplifying the second signal.

5. The device of claim 4 wherein the control circuit includes a differential amplifier for determining a difference between the first amplified signal and the second amplified signal and for amplifying the difference between the first amplified signal and the second amplified signal.

6. The device of claim 5 wherein the control circuit includes a comparator for comparing the amplified difference between the first amplified signal and the second amplified signal with a threshold and for generating an illumination signal if the amplified difference between the first amplified signal and the second amplified signal meets the threshold.

7. The device of claim 6 wherein the control circuit includes a light emitting diode, the light emitting diode generating the alert signal in response to the illumination signal.

8. A device for determining the wear of a sole of a shoe, comprising:
a first pressure sensor receivable in the sole of the shoe, the first sensor generating a first signal that is proportional to a first impact force acting thereon;
a second pressure sensor receivable in the sole of the shoe at a location vertically spaced from the first pressure sensor, the second sensor generating a second signal that is proportional to a second impact force acting thereon; and
a control circuit connectable to the first and second pressure sensors, the control circuit comparing the difference between the first and second signals to a threshold and generating an alert signal in response to the difference between the first and second signal meeting the threshold.

9. The device of claim 1 wherein the control circuit includes:
a first amplifier for amplifying the first signal; and
a second amplifier for amplifying the second signal.

10. The device of claim 9 wherein the control circuit includes a differential amplifier for determining the difference between the first amplified signal and the second amplified signal and for amplifying the difference between the first amplified signal and the second amplified signal.

11. The device of claim 10 wherein the control circuit includes a comparator for comparing the amplified difference between the first amplified signal and the second amplified signal with the threshold and for generating an illumination signal if the amplified difference between the first amplified signal and the second amplified signal meets the threshold.

12. The device of claim 11 wherein the control circuit includes a light emitting diode, the light emitting diode generating the alert signal in response to response to the illuminating signal.

13. The device of claim 8 wherein the control circuit is enclosed in a capsule.

14. A method for measuring the wear of a sole of a shoe, comprising the steps:
measuring an impact force exerted on a first portion of the sole of the shoe;
measuring an impact force exerted on a second portion of the sole of the shoe at a location vertically spaced from the first portion;
comparing the impact force exerted on the first portion of the shoe and the impact force exerted on the second portion of the shoe; and
generating an alert signal if the difference between the impact force exerted on the first portion of the shoe and the impact force exerted on the second portion of the shoe meets a threshold.

15. The method of claim 14 wherein the sole of the shoe includes a midsole affixed to an upper surface of an outsole and wherein the method includes the additional steps of:
positioning a first sensor between the outsole and the midsole to measure the impact force exerted on the first portion of the shoe; and
positioning a second sensor on an upper surface of the midsole to measure the impact force exerted on the second portion of the shoe.

16. The method of claim 15 wherein the first sensor and the second sensor are axially aligned.

17. The method of claim 15 wherein the step of comparing the impact force exerted on the first portion of the shoe and the impact force exerted on the second portion of the shoe includes the additional steps of:
generating a first signal that is proportional to a first impact force;
generating a second signal that is proportional to a second impact force acting thereon;
amplifying the first and second signals; and
determining the difference between the first amplified signal and the second amplified signal.

18. The method of claim 15 comprising the additional steps of:
providing a control circuit to compare the impact force exerted on the first portion of the shoe and the impact force exerted on the second portion of the shoe and to generate the alert signal; and
enclosing the control circuit in a capsule.

19. The method of claim 18 comprising the additional step of interconnecting the capsule to the shoe.

20. The method of claim 15 comprising the additional step of illuminating a light emitting diode in response to the alert signal.

* * * * *